(12) United States Patent
Wang et al.

(10) Patent No.: US 11,566,024 B2
(45) Date of Patent: Jan. 31, 2023

(54) TARTRATE OF SELECTIVE CDK9 INHIBITOR AND CRYSTAL FORM THEREOF

(71) Applicants: CHANGZHOU QIANHONG BIOPHARMA CO., LTD, Jiangsu (CN); CHANGZHOU LE SUN PHARMACEUTICALS LTD., Jiangsu (CN)

(72) Inventors: Shudong Wang, Adelaide (AU); Hui Wang, Jiangsu (CN); Liqun Jiang, Jiangsu (CN); Jinchen Lv, Jiangsu (CN); Wenjian Ju, Jiangsu (CN)

(73) Assignees: Changzhou Qianhong Biopharma Co., Ltd.; Changzhou Le Sun Pharmaceuticals Ltd.

( * ) Notice: Subject to any disclaimer, the term of this patent is extended or adjusted under 35 U.S.C. 154(b) by 31 days.

(21) Appl. No.: 17/253,785

(22) PCT Filed: May 29, 2019

(86) PCT No.: PCT/CN2019/088991
§ 371 (c)(1),
(2) Date: Dec. 18, 2020

(87) PCT Pub. No.: WO2019/242471
PCT Pub. Date: Dec. 26, 2019

(65) Prior Publication Data
US 2021/0139474 A1    May 13, 2021

(30) Foreign Application Priority Data

Jun. 20, 2018 (CN) .......................... 201810637484.9

(51) Int. Cl.
*C07D 417/04* (2006.01)

(52) U.S. Cl.
CPC ........ *C07D 417/04* (2013.01); *C07B 2200/13* (2013.01)

(58) Field of Classification Search
CPC .................................... C07D 417/04
USPC .......................................... 544/331
See application file for complete search history.

(56) References Cited

FOREIGN PATENT DOCUMENTS

| CN | 103373994 | 10/2013 |
| CN | 107118207 | 9/2017 |
| CN | 108658966 | 10/2018 |

OTHER PUBLICATIONS

Qin et al. "Salt type selection strategy in research and development of new drugs," Drugs & Clinic, Jul. 2012, vol. 27, No. 4, pp. 414-417 (English abstract).
International Search Report and Written Opinion for International (PCT) Patent Application No. PCT/CN2019/088991, dated Aug. 27, 2019, 9 pages.
English Translation of the International Search Report for International (PCT) Patent Application No. PCT/CN2019/088991, dated Aug. 27, 2019, 2 pages.

*Primary Examiner* — Kahsay Habte
(74) *Attorney, Agent, or Firm* — Sheridan Ross P.C.

(57) ABSTRACT

Disclosed are a tartrate of 3-(5-fluoro-4-(4-methyl-2-(methylamino)thiazol-5-yl) pyrimidin-2-ylamino)-benzenesulfonamide and a polymorph thereof, which are inhibitors of protein kinases, in particular cyclin-dependent kinase 9 (CDK9), and can be used to treat proliferative disorders, such as cancer, and other diseases related to protein kinase/CDK activity.

14 Claims, 8 Drawing Sheets

TARTRATE OF SELECTIVE CDK9 INHIBITOR AND CRYSTAL FORM THEREOF

CROSS REFERENCE TO RELATED APPLICATIONS

This application is a national stage application under 35 U.S.C. § 371 and claims the benefit of PCT Application No. PCT/CN2019/088991 having an international filing date of 29 May 2019, which designated the United States, which PCT application claimed the benefit of China Patent Application No. 201810637484.9 filed 20 Jun. 2018, the disclosures of each of which are incorporated herein by reference in their entireties.

TECHNICAL FIELD

The present invention relates to the field of chemical pharmaceutical technologies, in particular to a salt form of 3-(5-fluoro-4-(4-methyl-2-(methylamino) thiazol-5-yl) pyrimidin-2-ylamino)-benzenesulfonamide and a stable crystal form thereof, which are selective inhibitors of Cyclin-Dependent Kinases (CDKs), such as CDK9, and which may be used to treat cell proliferative disorders, such as cancer.

TECHNICAL BACKGROUND

The characteristic of proliferative disorders, such as cancer, is uncontrolled and irregular cell proliferation. The family of protein kinases has become a type of important enzymes as the subject of extensive research in this aspect. The family of protein kinases is one of the largest families in the human genome. Most of the kinases contain a catalytic domain of 250-300 amino acid residues with a conserved core structure. This domain comprises an ATP-binding pocket, and the terminal phosphate group of the ATP is transferred covalently to a macromolecular substrate thereof. The protein kinases may be categorized according to substrates of phosphorylation thereof, such as protein-serine/threonine and protein-tyrosine.

The protein kinases mediate intracellular signaling by causing a phosphoryl group to be transferred from nucleoside triphosphate to a protein receptor involved in a signaling pathway. These phosphorylation events are triggered in response to a variety of extracellular stimuli and other stimuli, and act as molecular switches that can modulate or regulate biological functions of a target protein. An extracellular stimulus may affect one or more cellular responses related to cell growth, migration, differentiation, hormone secretion, activation of transcription factors, muscle contraction, glucose metabolism, protein synthesis control, and cell cycle regulation.

A variety of diseases are associated with abnormal cellular responses triggered by protein kinase-mediated events. These diseases include, but are not limited to, allergy and asthma, Alzheimer's disease, autoimmune diseases, bone diseases, cancer, cardiovascular diseases, inflammatory diseases, hormone-related diseases, metabolic diseases, neurological diseases, and neurodegenerative diseases. Therefore, tremendous effort has been made in the field of pharmaceutical chemistry to find protein kinase inhibitors that act effectively as therapeutic agents.

Numerous molecules capable of inhibiting protein kinase functions through antagonizing ATP binding are known in the prior art. CDKs are serine/threonine protein kinases associated with a variety of cyclin subunits and play a key role in the regulation of cell cycle process and transcription cycle. Ten different CDKs (CDK1-9 and 11) are involved in a variety of important regulatory pathways in eukaryotic cells, including cell cycle control, apoptosis, neuronal physiology, differentiation, and transcription.

CDKs may be classified into two major groups reflecting functions thereof. Cell cycle regulator CDKs primarily consisting of CDK1, CDK2, CDK3, CDK4, and CDK6 act together with their cyclin partners (including cyclins A, B, D1, D2, D3, E, and F) to regulate promotion of the cell cycle. Transcription regulator CDKs comprising CDK7, CDK8, CDK9, and CDK11 work together with cyclins C, H, K, L1, L2, T1, and T2 and tend to play a role in transcription regulation. CDKs have been involved in cell proliferative disorders, in particular in cancer. Cell proliferation is a result of a cell division cycle that is directly or indirectly out of control, and CDKs play a key role in the regulation of multiple phases of the cycle. Therefore, inhibitors of CDKs and their associated cyclins are useful targets for cancer treatment. CDKs also play a role in apoptosis and T-cell development, which is mainly because of functions of CDK in transcription regulation. For example, specific clinical activity has been obtained in recent application of CDK inhibitor flavopiridol in Chronic Lymphocytic Leukemia (CLL). The characteristic of CLL is cellular resistance to apoptosis through up-regulation of anti-apoptotic proteins. Inhibition of transcription at the CDK9 level (which is required by mRNA elongation) selectively reinstates apoptosis in CLL cells. However, there is still a need for pharmacologically and pharmaceutically better CDK inhibitors with well-defined kinase selectivity and cellular specificity, anti-CLL efficacy, and efficacy of antagonizing other CDK mediated disorders.

In addition, replication processes of numerous viruses require CDKs, in particular CDK2, CDK7, and CDK9. CDK inhibitors that restrain viral replication including human immunodeficiency virus, human cytomegalovirus, herpes virus, and varicella-zoster virus have been reported. Inhibition of CDKs, in particular CDK9, is a novel strategy for potential treatment of cardiovascular diseases, including cardiac hypertrophy. The characteristic of cardiac hypertrophy is the overall increase of mRNA and protein synthesis. CDK7 and CDK9 are closely related to cardiac hypertrophy, as they are major drivers for transcription. Therefore, inhibition of CDK9 and its associated cyclins is a relevant drug target for cardiovascular diseases.

Inhibition of CDKs may also be used for treatment of neurodegenerative disorders such as Alzheimer's disease. The presence of Paired Helical Filaments associated with Alzheimer's disease is caused by hyperphosphorylation of Tau proteins by CDK5/p25.

Chinese invention patent with Publication No. CN103373994A (which is incorporated herein by reference in its entirety) discloses a type of compounds with CDK-9 inhibition capability and a preparation method therefor, wherein pharmaceutically acceptable salts of the compounds are mentioned, but no salts of specific compound are prepared, nor are types and properties of the salts further evaluated.

Therefore, there is still a need for identifying new therapeutic agents that can be used to treat such conditions. In particular, there is a need for identifying other compounds that function as inhibitors of activity of protein kinases (and in particular CDKs) and further comprise one or more advantageous pharmaceutical properties. The one or more advantageous pharmaceutical properties may be selected from increased potency/target activity (e.g., increased antiproliferative activity), increased therapeutic efficacy (e.g., increased activity against certain cancer cell lines and/or improved selectivity against cancer cells), and/or improved bioavailability (e.g., oral bioavailability) and the like.

Formula I

SUMMARY OF THE INVENTION

The present invention provides a tartrate form of 3-(5-fluoro-4-(4-methyl-2-(methylamino)thiazol-5-yl) pyrimidin-2-ylamino)-benzenesulfonamide as represented by Formula II:

Formula II

The tartrate may be present in one or more polymorphic forms, including Form A and Form B. The polymorphic forms may be differentiated through X-ray powder diffraction patterns, Raman spectra, or DSC thermograms thereof.

One aspect of the present invention provides a 3-(5-fluoro-4-(4-methyl-2-(methylamino)thiazol-5-yl) pyrimidin-2-ylamino)-benzenesulfonamide tartrate designated as Crystal Form A, characterized by one or more of the following: a X-ray powder diffraction pattern with peaks located at positions with 2θ values of about 9.6, 18.9, 24.5, and 26.7 and with no peaks located at positions with 2θ values of 8.1, 10.6, 14.9, and 16.1, a Raman spectrum with peaks located at positions with Raman shift values of about 1389 $cm^{-1}$, 1503 $cm^{-1}$, 1571 $cm^{-1}$, and 1597 $cm^{-1}$ and with no peaks located at positions with Raman shift values of about 806 $cm^{-1}$ and 1569 $cm^{-1}$, or a DSC thermogram with a sharp endothermic peak at 238.6° C.

Another aspect of the present invention provides a 3-(5-fluoro-4-(4-methyl-2-(methylamino)thiazol-5-yl) pyrimidin-2-ylamino)-benzenesulfonamide tartrate designated as Crystal Form B, characterized by one or more of the following: a X-ray powder diffraction pattern with peaks located at positions with 2θ values of about 8.1, 10.6, 14.9, and 16.1, a Raman spectrum with peaks located at positions with Raman shift values of about 297 $cm^{-1}$, 325 $cm^{-1}$, 806 $cm^{-1}$, and 1569 $cm^{-1}$, a DSC thermogram with a sharp endothermic peak at 239.9° C., or an infrared spectrogram with peaks at shifts of 1641 $cm^{-1}$ and 3355 $cm^{-1}$. For the various salt forms, the X-ray powder diffraction patterns are obtained using CuKα radiation, and the DSC thermograms are obtained using a heating rate of 10° C./min.

The present invention further provides a method for preparing the Crystal Form A of 3-(5-fluoro-4-(4-methyl-2-(methylamino)thiazol-5-yl)pyrimidin-2-ylamino)-benzenesulfon amide tartrate, characterized by the following steps:

(1) mixing 3-(5-fluoro-4-(4-methyl-2-(methylamino)thiazol-5-yl)pyrimidin-2-ylamino)-benzenesulfonamide and a certain amount of dimethyl sulfoxide as a solvent, and heating to dissolve to obtain a first mixture;

(2) adding a certain amount of tartaric acid and water to the first mixture, and reacting to obtain a second mixture; and (3) adding a certain amount of a water-miscible solvent to the second mixture, and reacting to obtain 3-(5-fluoro-4-(4-methyl-2-(methylamino)thiazol-5-yl) pyrimidin-2-ylamino)-benzenesulfonamide tartrate, which is the Crystal Form A of the tartrate.

In the above method, the second mixture is obtained by mixing tartaric acid and 3-(5-fluoro-4-(4-methyl-2-(methylamino)thiazol-5-yl) pyrimidin-2-ylamino)-benzenesulfonamide at a molar ratio of 1.1 to 1.3:1, the water-miscible solvent in step (3) is an alcohol, and the alcohol is ethanol.

Preferably, the reaction time in step (2) is 0.1 to 3 hours.

Preferably, the reaction time in step (3) is 1 to 10 hours.

The present invention further provides a use of the above 3-(5-fluoro-4-(4-methyl-2-(methylamino) thiazol-5-yl) pyrimidin-2-ylamino)-benzenesulfonamide tartrate and the Crystal Form A thereof in the preparation of a medicine for treatment of proliferative disorders, wherein the conditions caused by proliferative disorders are cancer, and furthermore, the cancer includes acute myeloid leukemia.

The present invention further provides a use of the above 3-(5-fluoro-4-(4-methyl-2-(methylamino) thiazol-5-yl) pyrimidin-2-ylamino)-benzenesulfonamide tartrate and the Crystal Form A thereof in the preparation of a medicine for inhibiting a protein kinase.

With respect to the free base (Formula I) and other salt forms including hydrochlorides, maleates, phosphates, and the like, the tartrate provides many advantages. Compared with the free base, the water solubility of the tartrate is improved by 40 times. However, unlike phosphates and the like, the above increase in solubility is not accompanied by a significant increase in hygroscopicity. In preliminary stability tests, the tartrate has shown better stability under conditions of high temperature, high humidity, and illumination. Moreover, the tartrate has good crystallinity and is easy for scale-up of the production. The above and other advantages will be favorable for overcoming various challenges faced by the development of pharmaceutical products containing selective CDK 9 kinase inhibitors of Formula I.

BRIEF DESCRIPTION OF THE DRAWINGS

Various features, advantages, and other applications of the present invention will be more obvious with reference to the description below and the accompanying drawings.

DETAILED DESCRIPTION

Definitions

The term "cancer" includes, but is not limited to, the following cancers: leukemia, breast cancer, ovarian cancer, cervical cancer, prostate cancer, testicular cancer, esophageal cancer, gastric cancer, skin cancer, lung cancer, bone cancer, colon cancer, pancreatic cancer, thyroid cancer, biliary tract cancer, throat cancer, lip cancer, tongue cancer, oral cancer, throat cancer, small intestine cancer, colon-rectal cancer, colorectal cancer, rectal cancer, brain and central nervous system cancer, malignant glioma, bladder cancer, liver cancer, kidney cancer, lymphoma, and the like.

3-(5-fluoro-4-(4-methyl-2-(methylamino) thiazol-5-yl) pyrimidin-2-ylamino)-benzenesulfonamide tartrate (Formula II) can be present in one or more polymorphic forms, including Form A and Form B. As described above, the polymorphic forms may be differentiated through X-ray powder diffraction, Raman spectroscopy, infrared spectroscopy, differential scanning calorimetry, or some combination of these characterization methods. The tartrate (Formula II) may be of high purity, i.e., containing at least 99% by weight of a particular polymorph, or may be a mixture of two polymorphs.

Figure 1:
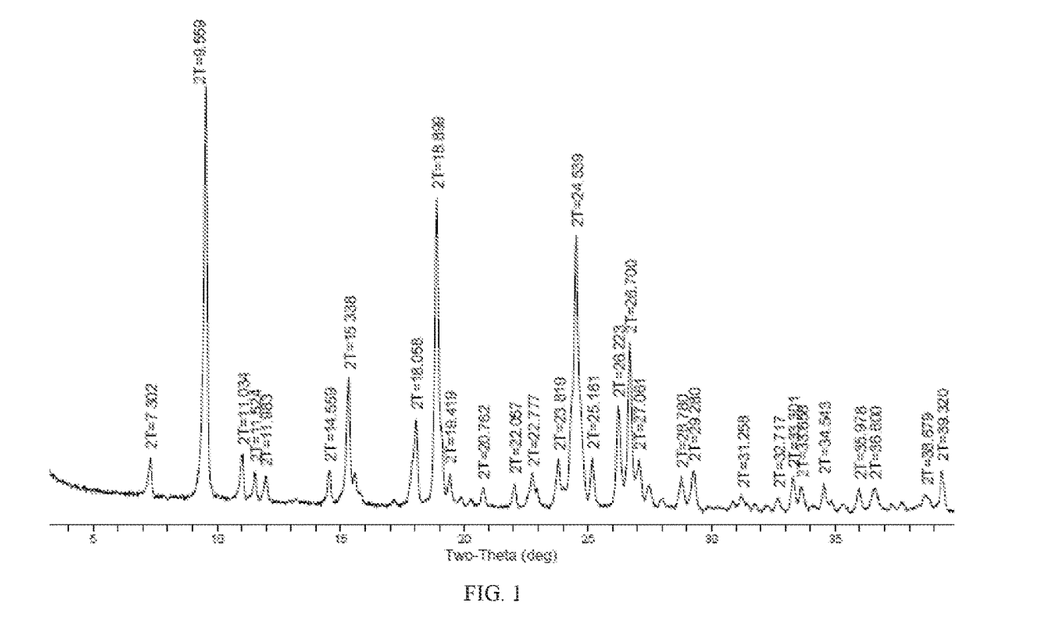
FIG. 1 is an X-ray powder diffraction pattern of Crystal Form A of 3-(5-fluoro-4-(4-methyl-2-(methylamino) thiazol-5-yl) pyrimidin-2-ylamino)-benzenesulfonamide tartrate.
Figure 2:
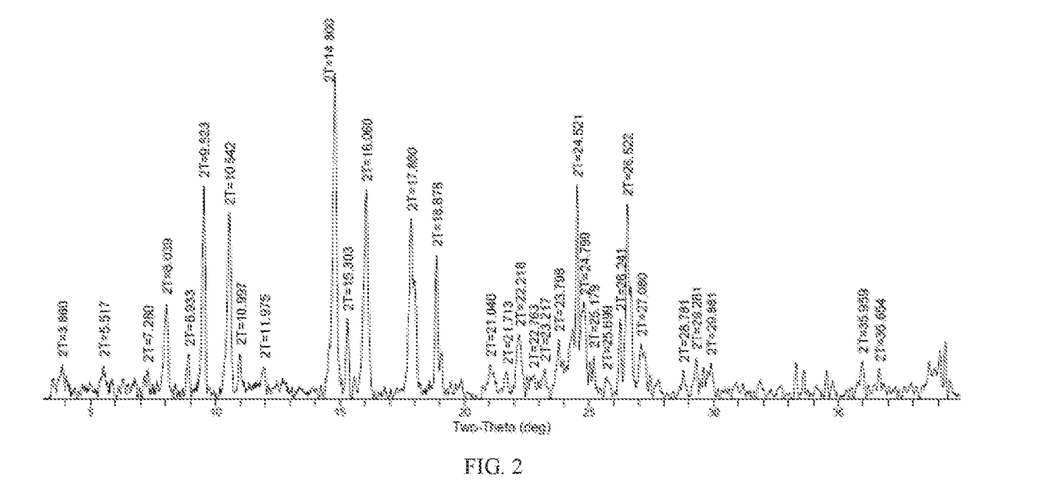
FIG. 2 is an X-ray powder diffraction pattern of Crystal Form B of 3-(5-fluoro-4-(4-methyl-2-(methylamino) thiazol-5-yl) pyrimidin-2-ylamino)-benzenesulfonamide tartrate.
Figure 3:
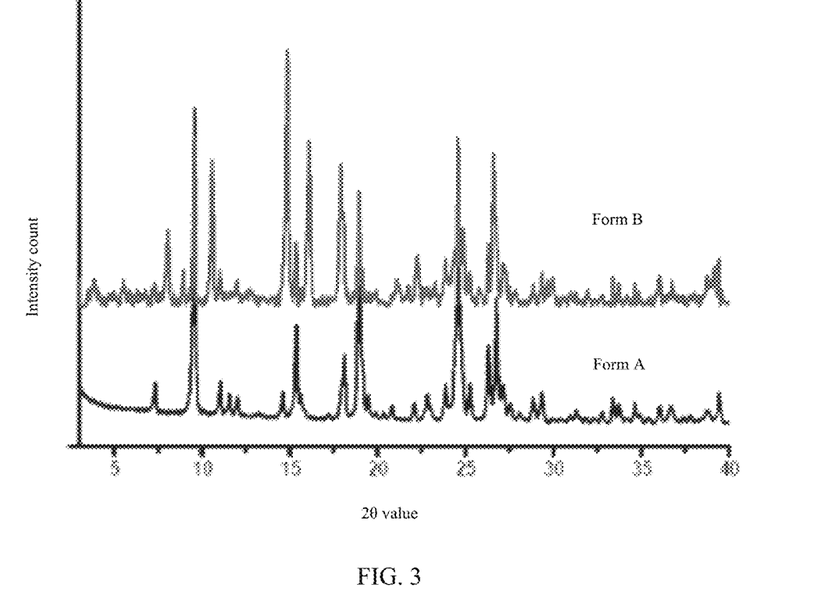
FIG. 3 is an overlay of X-ray powder diffraction patterns of Crystal Form A and Crystal Form B of 3-(5-fluoro-4-(4-methyl-2-(methylamino) thiazol-5-yl) pyrimidin-2-ylamino)-benzenesulfonamide tartrate with 2θ values in a range from 0 to 40.
Figure 4:
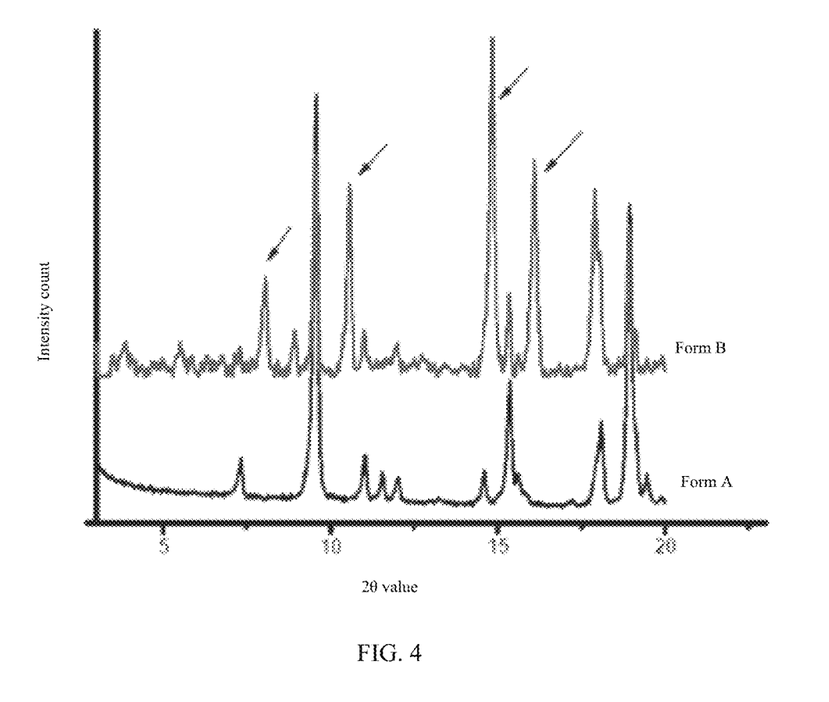
FIG. 4 is an overlay of X-ray powder diffraction patterns of Crystal Form A and Crystal Form B of 3-(5-fluoro-4-(4-methyl-2-(methylamino) thiazol-5-yl) pyrimidin-2-ylamino)-benzenesulfonamide tartrate with 2θ values in a range from 0 to 20.
Figure 5:
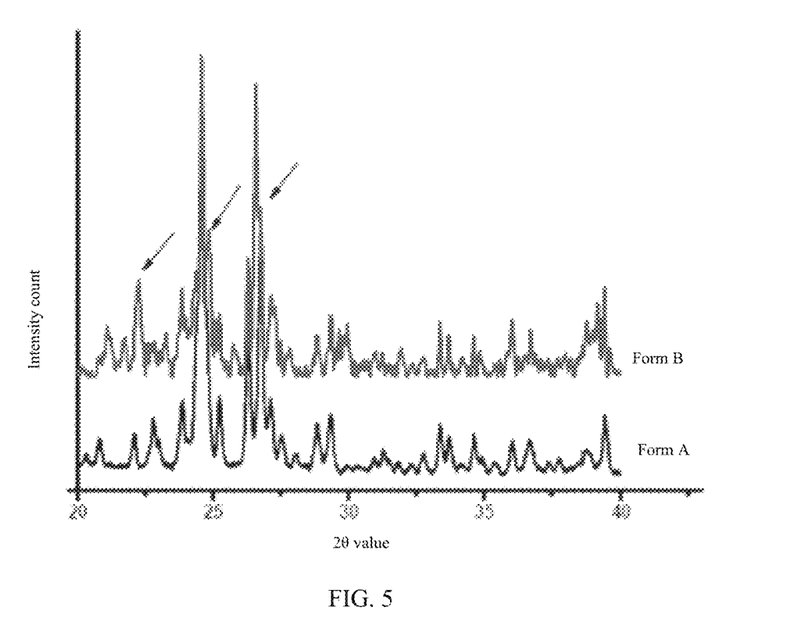
FIG. 5 is an overlay of X-ray powder diffraction patterns of Crystal Form A and Crystal Form B of 3-(5-fluoro-4-(4-methyl-2-(methylamino) thiazol-5-yl) pyrimidin-2-ylamino)-benzenesulfonamide tartrate with 2θ values in a range from 20 to 40.

FIG. 1 and FIG. 2 provide X-ray powder diffraction patterns of 3-(5-fluoro-4-(4-methyl-2-(methylamino) thiazol-5-yl) pyrimidin-2-ylamino)-benzenesulfonamide tartrate (Formula II), which define these polymorphic forms as Form A in FIG. 1 and Form B in FIG. 2. In order to facilitate comparison and reading, FIG. 3 is an overlay of X-ray powder diffraction patterns of Crystal Form A and Crystal Form B, and FIG. 4 and FIG. 5 are partially enlarged views of the overlay, respectively. Through comparison of the enlarged views, Polymorphic Form B is significantly different from Form A at 8.1, 10.6, 14.9, 16.1, etc. A person of ordinary skills in the field of polymorph identification is able to distinguish one crystal form from another crystal form by superimposing and comparing X-ray powder diffraction patterns and selecting a combination of characteristic peaks.

The X-ray powder diffraction patterns shown in FIG. 1 to FIG. 5 are obtained on a Bruker D8 advance X-ray powder diffractometer using CuKα (40 kV, 40 mA) radiation. When the diffractometer is operated, the tube voltage and current are set to 40 kV and 40 mA, respectively, the distance from a sample to the detector: 30 cm, the scanning step: 0.1 s, and the scanning range: 3° to 40° (2θ).

Figure 6:
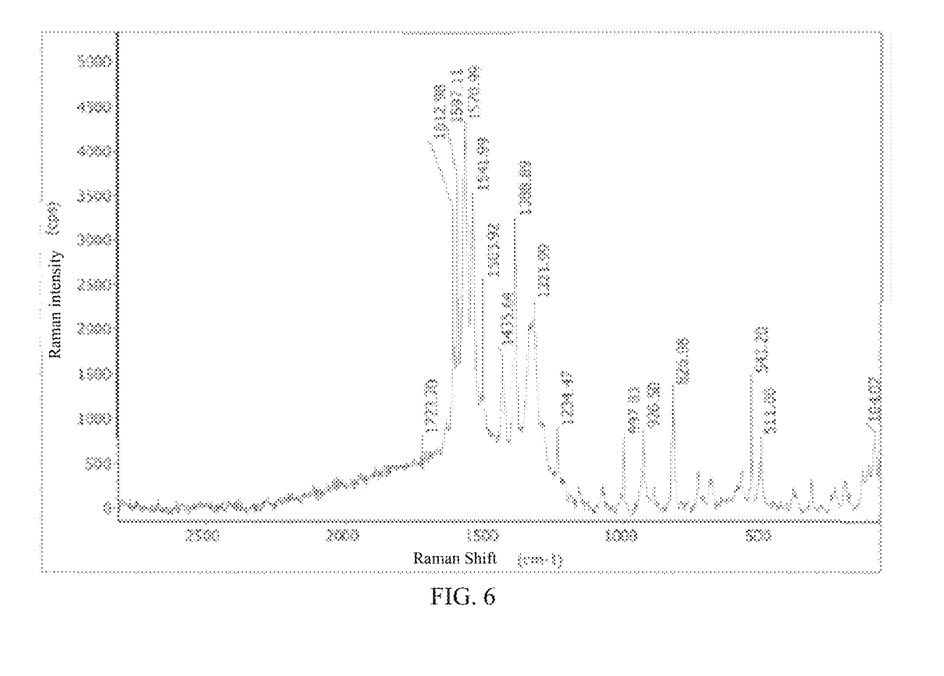
FIG. 6 is an overlay of Raman spectra of Crystal Form A of 3-(5-fluoro-4-(4-methyl-2-(methylamino) thiazol-5-yl) pyrimidin-2-ylamino)-benzenesulfonamide tartrate with Raman shift values in a range from 0 cm$^{-1}$ to 3000 cm$^{-1}$.
Figure 7:
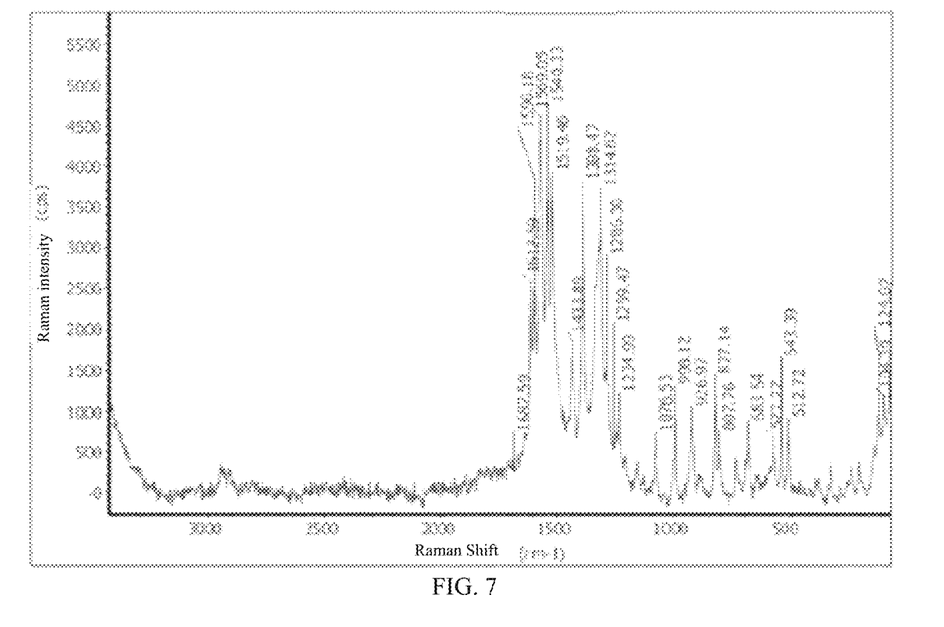
FIG. 7 is an overlay of Raman spectra of Crystal Form B of 3-(5-fluoro-4-(4-methyl-2-(methylamino) thiazol-5-yl) pyrimidin-2-ylamino)-benzenesulfonamide tartrate with Raman shift values in a range from 0 cm$^{-1}$ to 3000 cm$^{-1}$.
Figure 8:
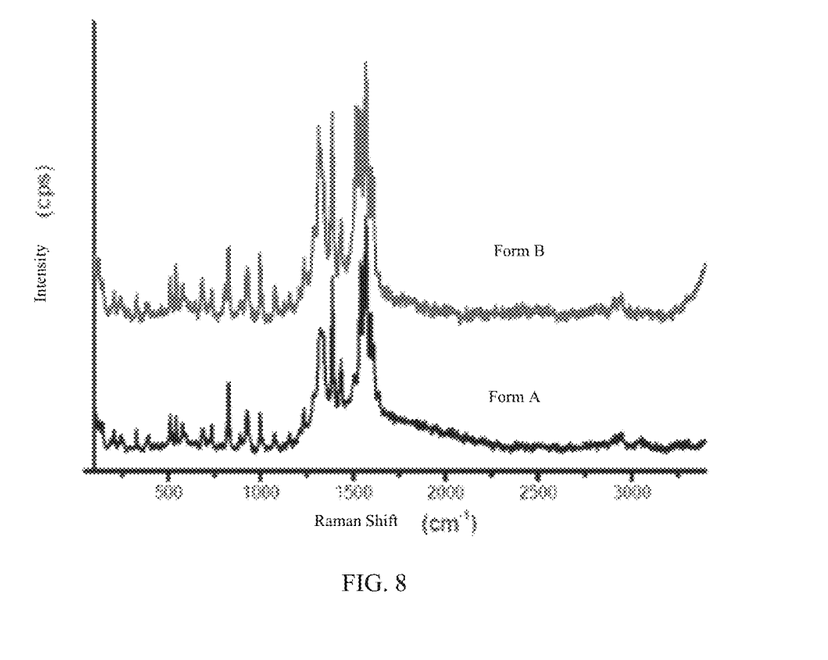
FIG. 8 is an overlay of Raman spectra of Crystal Form A and Crystal Form B of 3-(5-fluoro-4-(4-methyl-2-(methylamino) thiazol-5-yl) pyrimidin-2-ylamino)-benzenesulfonamide tartrate with Raman shift values in a range from 0 cm$^{-1}$ to 3000 cm$^{-1}$.
Figure 9:
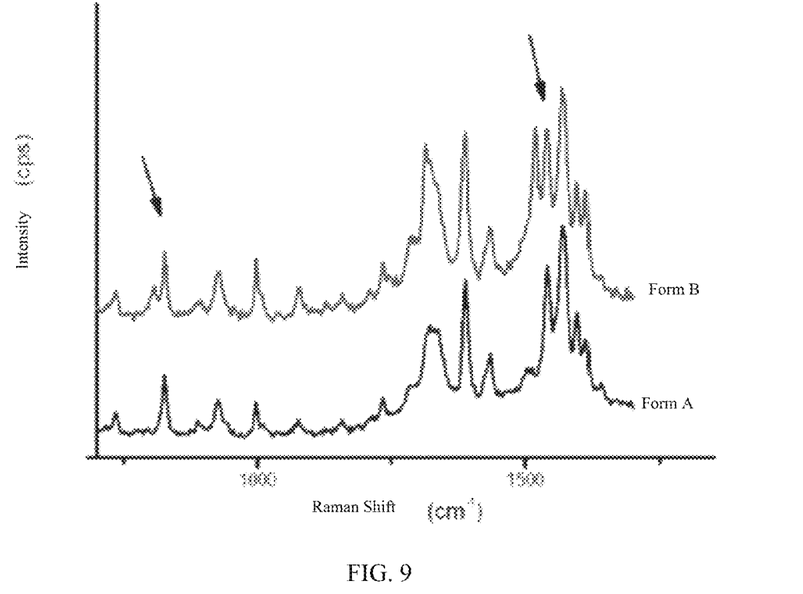
FIG. 9 is an overlay of Raman spectra of Crystal Form A and Crystal Form B of 3-(5-fluoro-4-(4-methyl-2-(methylamino) thiazol-5-yl) pyrimidin-2-ylamino)-benzenesulfonamide tartrate with Raman shift values in a range from 750 cm$^{-1}$ to 1750 cm$^{-1}$.
Figure 10:
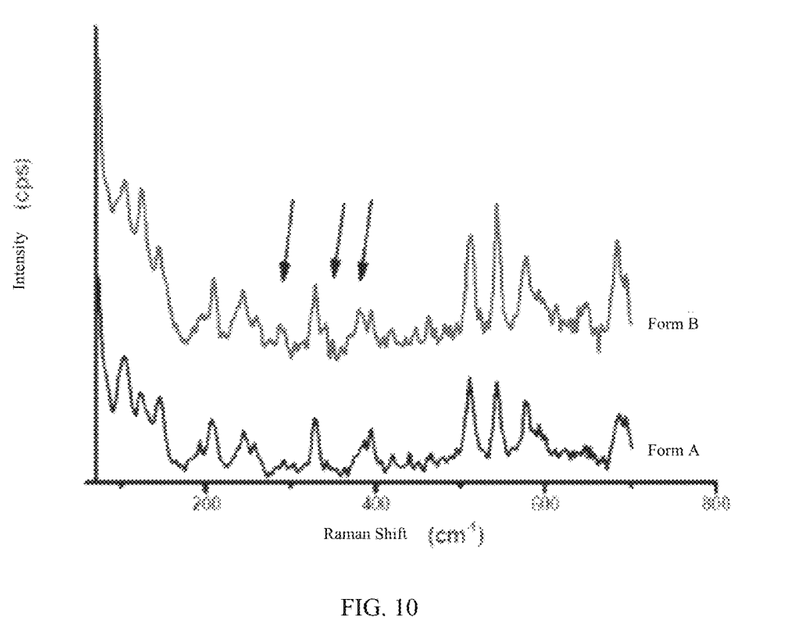
FIG. 10 is an overlay of Raman spectra of Crystal Form A and Crystal Form B of 3-(5-fluoro-4-(4-methyl-2-(methylamino) thiazol-5-yl) pyrimidin-2-ylamino)-benzenesulfonamide tartrate with Raman shift values in a range from 100 cm$^{-1}$ to 800 cm$^{-1}$.

FIGS. 6-10 provide Raman spectra of 3-(5-fluoro-4-(4-methyl-2-(methylamino) thiazol-5-yl) pyrimidin-2-ylamino)-benzenesulfonamide tartrate (Formula II). FIG. 6 and FIG. 7 provide Raman spectra of Crystal Form A and Crystal Form B of the tartrate, respectively, wherein the Raman shift is from 0 $cm^{-1}$ to 3000 $cm^{-1}$. For convenience of comparison and reading, FIG. 8 is an overlay of Raman spectra of Crystal Form A and Crystal Form B. FIG. 9 and FIG. 10 are partially enlarged views of the overlay, respectively. Through comparison of the enlarged views, Polymorphic Form B is significantly different from Form A at 297 $cm^{-1}$, 325 $cm^{-1}$, 806 $cm^{-1}$, and 1569 $cm^{-1}$. A person of ordinary skills in the field of polymorph identification is able to distinguish one polymorphic form from another polymorphic form by choosing the above characteristic data or other characteristics.

Figure 11:
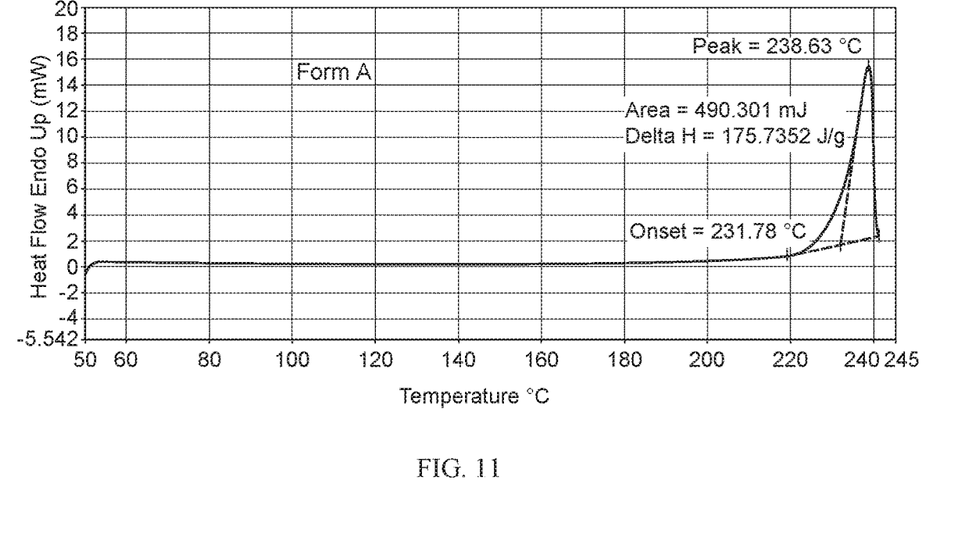
FIG. 11 is a DSC thermogram of Crystal Form A of 3-(5-fluoro-4-(4-methyl-2-(methylamino) thiazol-5-yl) pyrimidin-2-ylamino)-benzenesulfonamide tartrate.
Figure 12:
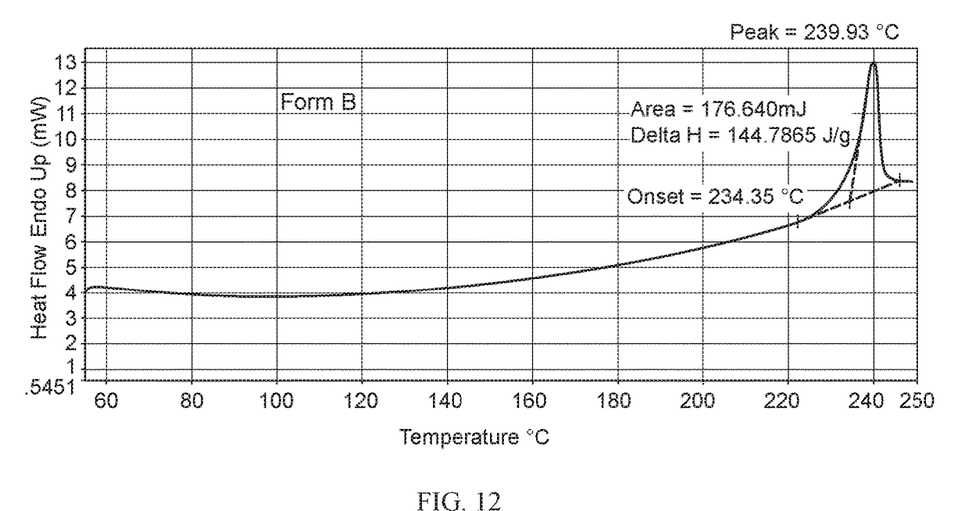
FIG. 12 is a DSC thermogram of Crystal Form B of 3-(5-fluoro-4-(4-methyl-2-(methylamino) thiazol-5-yl) pyrimidin-2-ylamino)-benzenesulfonamide tartrate.

FIG. 11 and FIG. 12 respectively provide DSC thermograms of 3-(5-fluoro-4-(4-methyl-2-(methylamino) thiazol-5-yl) pyrimidin-2-ylamino)-benzenesulfonamide tartrate (Formula II) designated as Polymorphic Form A and Form B. The DSC data is obtained using a Perkin Elmer DSC 8500, temperature range: 50-280° C., scan rate: 10° C./min, and nitrogen flow rate: 20 mL/min. The DSC spectra show that Crystal Form A and Form B are heated to melt and decompose, and the two have similar melting points. Form A has a sharp endothermic peak at 238.6° C., and Form B has a sharp endothermic peak at 239.9° C.

Figure 13:
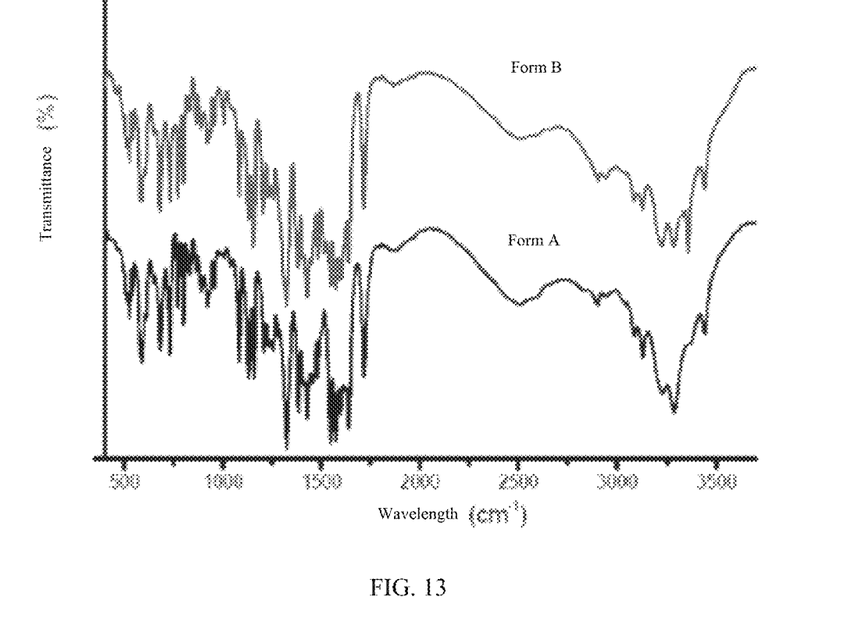
FIG. 13 is an overlay of infrared spectra of Crystal Form A and Crystal Form B of 3-(5-fluoro-4-(4-methyl-2-(methylamino) thiazol-5-yl) pyrimidin-2-ylamino)-benzenesulfonamide tartrate with infrared shift values in a range from 500 cm$^{-1}$ to 3500 cm$^{-1}$.
Figure 14:
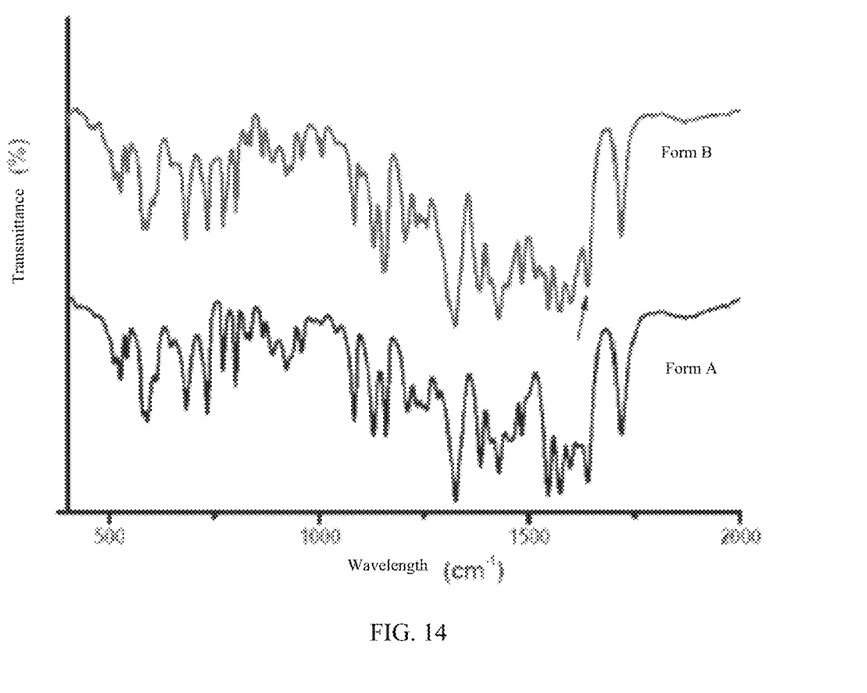
FIG. 14 is an overlay of infrared spectra of Crystal Form A and Crystal Form B of 3-(5-fluoro-4-(4-methyl-2-(methylamino) thiazol-5-yl) pyrimidin-2-ylamino)-benzenesulfonamide tartrate with infrared shift values in a range from 500 cm$^{-1}$ to 2000 cm$^{-1}$.
Figure 15:
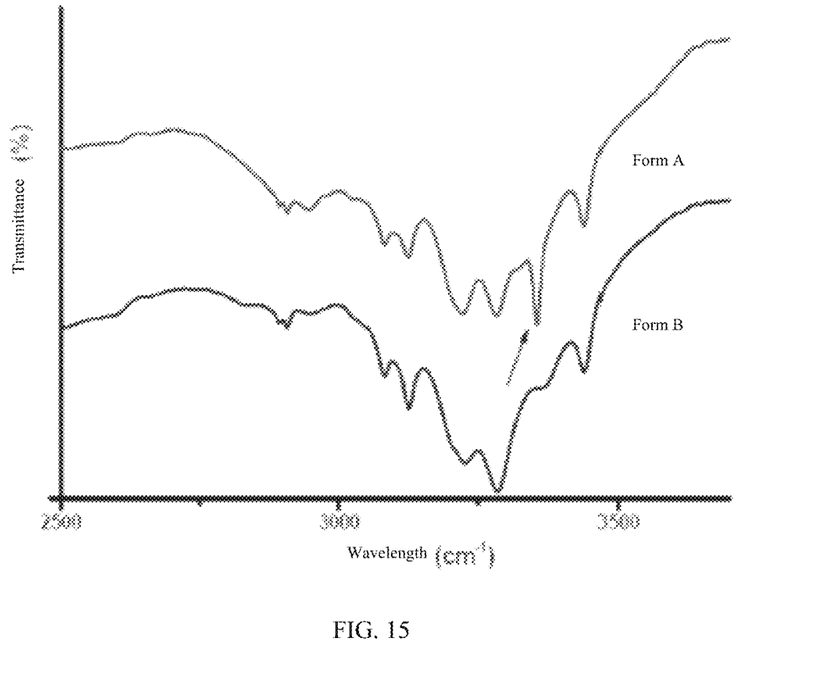
FIG. 15 is an overlay of infrared spectra of Crystal Form A and Crystal Form B of 3-(5-fluoro-4-(4-methyl-2-(methylamino) thiazol-5-yl) pyrimidin-2-ylamino)-benzenesulfonamide tartrate with infrared shift values in a range from 2500 cm$^{-1}$ to 3000 cm$^{-1}$.

FIGS. 13-15 provide the infrared spectra of 3-(5-fluoro-4-(4-methyl-2-(methylamino) thiazol-5-yl) pyrimidin-2-ylamino)-benzenesulfonamide tartrate (Formula II). For convenience of comparison and reading, FIGS. 13-15 are all superimposed comparison diagrams of Crystal Form A and Form B. The infrared shift on FIG. 13 is 500 $cm^{-1}$ to 3500 $cm^{-1}$, the infrared shift on FIG. 14 is 500 $cm^{-1}$ to 2000 $cm^{-1}$, and the infrared shift on FIG. 15 is 2500 $cm^{-1}$ to 3000 $cm^{-1}$. It can be seen from the comparison of the overlay of infrared spectra that Polymorphic Form B is significantly different from Form A at 1641.1 $cm^{-1}$, 3355.5 $cm^{-1}$, and the like.

SPECIFIC IMPLEMENTATIONS

The present invention will be further described in detail below in combination with examples, but is not limited thereto.

Example 1 Salt Formation Properties of 3-(5-fluoro-4-(4-methyl-2-(methylamino) Thiazol-5-yl) Pyrimidin-2-ylamino)-benzenesulfonamide Tartrate (with a Designation of LS007)

1.1 High-Throughput Screening of Salt Formation

Based on the pKa value and solubilities at different pH of LS007, it can be determined that acids with pKa values of about 3 or lower may be used as acids for salt formation screening. Therefore, we selected 8 acids, including hydrochloric acid, sulfuric acid, aspartic acid, maleic acid, phosphoric acid, glutamic acid, tartaric acid, and fumaric acid.

Dissolve the medicine and then add it to a 96-well plate, and determine the amount of counter ion to be added according to the molar mass of the added medicine and the quantity of the counter-ion functional groups. The heating time and temperature may be determined according to specific situation (typically 40° C. and 1 hour). In order to ensure a certain pressure in the flask during the reaction, the absolute tightness of a sample must be ensured during the mixing, vortex, and heating processes, and there must be at least a silicon resin liner throughout the entire process. The specific steps are as follows:

1) preparing a 0.02 M THF solution of the acids, wherein glutamic acid, sulfuric acid, and phosphoric acid are aqueous solutions;

2) preparing a 0.01 M THF/MeOH (1:1) solution of LS007;

3) adding 1 mL of hydrochloric acid, 0.25 mL of sulfuric acid, 0.5 mL of aspartic acid, 0.5 mL of maleic acid, 0.5 mL of phosphoric acid, 0.5 mL of glutamic acid, 0.5 mL of tartaric acid, and 0.5 mL of fumaric acid, and then adding 1 mL solution of LS007, respectively; and 4) after vortex, reacting in a 40° C. oil bath for 1 hour, evaporating the organic solvent at room temperature, and finally reducing pressure for drying at 50° C.

A comparison of Raman spectra shows that hydrochloric acid, sulfuric acid, phosphoric acid, maleic acid, tartaric acid, and fumaric acid all form a salt with LS007, while aspartic acid and glutamic acid do not form a salt.

Perform scale-up experiments on the above six salts to determine solubilities of various salts in different pH buffers and deionized water, and compare with the free base. The results are listed in Table 1:

TABLE 1

|  | LS007 | Hydrochloride | Sulfate | Phosphate | Maleate | Fumarate | Tartrate |
| --- | --- | --- | --- | --- | --- | --- | --- |
| Glycine-HCl buffer (pH 2.0) | 134.1 | 904.4 | 141.8 | 1116.6 | 98.2 | 48.1 | 4302.3 |
| Na$_2$HPO$_4$-citric acid buffer (pH 4.5) | 3.6 | 7.3 | 1.9 | 1.7 | 4.2 | 2.9 | 7.5 |
| Na$_2$HPO$_4$-citric acid buffer (pH 6.8) | 1.4 | 3.9 | 1.9 | 2.9 | 9.1 | 1.8 | 3.7 |
| Deionized water | 9.6 | 405.1 | 69.7 | 412.1 | 75.8 | 35.7 | 418.1 |

Select the hydrochloride, phosphate, and tartrate with relatively good solubilities, and perform comprehensive solid-state characterization on the free base LS007, hydrochloride, phosphate, and tartrate. The comparison results are listed in Table 2:

TABLE 2

| Properties | LS007 | Hydrochloride | Phosphate | Tartrate |
|---|---|---|---|---|
| Appearance | | | | |
| Melting point | | | | |
| TGA (decomposition temperature) | | | | |
| Solubility (25° C., | 134.1 | 904.4 | 1116.6 | 4302.3 |
| Glycine-HCl buffer (pH 2.0) | 3.6 | 7.3 | 1.7 | 7.5 |
| $Na_2HPO_4$-citric acid buffer (pH 4.5) | 1.4 | 3.9 | 2.9 | 3.7 |
| $Na_2HPO_4$-citric acid buffer (pH 6.8) | 9.6 | 405.1 | 412.1 | 418.1 |
| Deionized water | | | | |
| pH (saturated aqueous solution 25° C.) | 3.06 | 2.70 | 2.50 | 3.03 |
| Hygroscopicity (DVS, 60% RH) | 1.20 | 2.39 | 11.71 | 1.36 |

The solubility results from HPLC testing show that the solubilities of the hydrochloride, phosphate, and tartrate in the pH 2.0 buffer and deionized water are significantly increased compared to those of the raw materials. Solubility: tartrate>phosphate>hydrochloride>free base.

It can be seen from the DVS experiments on the Active Pharmaceutical Ingredients that LS007 has very low hygroscopicity, and hygroscopicity is increased after salt formation, wherein the phosphate has the highest hygroscopicity and absorbs 11.71% of water at 60% RH, followed by the hydrochloride, and the tartrate has the lowest hygroscopicity.

The inventors are surprised to find that the tartrate has extraordinary performance in both solubility and hygroscopicity.

Example 2 Crystal Forms of 3-(5-fluoro-4-(4-methyl-2-(methylamino) Thiazol-5-yl) pyrimidin-2-ylamino)-benzenesulfonamide Tartrate For the polymorph issue of LS007 tartrate, this study has systematically screened possible crystal forms of compound LS007 tartrate by using different crystallization conditions and experimental approaches. Through nearly 300 crystallization experiments, it has been found that LS007 tartrate can exist in two different crystal forms, Crystal Form A and Crystal Form B, respectively. Further characterization has revealed that there is no significant difference in physicochemical properties between the different crystal forms. In the conversion experiments between the crystal forms, it has been found that Form A is a more stable crystal form, and Form B can be converted to Crystal Form A under certain conditions.

(1) Form A

Column-shaped crystal, melt and decompose the medicine, and the decomposition peak temperature is 236.8° C. It is non-hygroscopic (at 80% humidity, the hygroscopic weight gain is 0.22%). The amplitude of variation of humidity is low within a conventional storage humidity range. The physical and chemical properties are relatively ideal, the sample has the best crystallinity, the fluidity is greater than that of Form B, and the drug formation performance is better than that of Form B. Moreover, the equilibrium solubility is greater than that of Form B under various simulated in vivo conditions (pH=2.0, 4.6, 6.8).

The specific preparation method of Crystal Form A is as follows:

Add LS007 free base and dimethyl sulfoxide in a mass 6 times the mass of the free base into a four-necked flask, heat to completely dissolve (control the temperature <60° C.), and filter while hot; transfer the reaction mixture to a 10 L reaction flask, and add tartaric acid at 0.494 times (the weight of the free base, 1.3 equivalents) and water at 0.27 times (the weight of the free base), stir, heat to 60±2° C. and keep the temperature constant for half an hour; add anhydrous ethanol at 8.6 times (the weight of the free base), and keep the temperature constant at 60±2° C. for 4 hours; and lower the system temperature to 25±5° C., filter through suction (or centrifuge to dry), and wash the filter cake with an appropriate amount of anhydrous ethanol.

Add the above solid and anhydrous ethanol 2-3 times the mass of the solid into the flask, stir at 80° C. for 1 hour, filter while hot, and dry the obtained filter cake with hot air at 80° C. to obtain a product as a yellow solid, which is the Crystal Form A of LS007 tartrate.

(2) Form B

Granular crystal, melt and decompose the medicine, and the decomposition peak temperature is 240.5° C. It is non-hygroscopic (at 80% humidity, the hygroscopic weight gain is 0.11%). The amplitude of variation of humidity is low within a conventional storage humidity range. Form B can be obtained when $NM:H_2O$ (1:1) is used as a solvent in a suspension experiment at 50° C.

It can be seen from the XRPD overlay that Form B is significantly different from Form A at 8.08°, 10.63°, 14.85°, 16.12°, 22.30°, 24.33°, 26.50°, etc.

All reference documents mentioned in the present invention are referenced in the present application, as if each reference document is individually referenced.

The invention claimed is:

1. A 3-(5-fluoro-4-(4-methyl-2-(methylamino)thiazol-5-yl) pyrimidin-2-ylamino)-benzenesulfonamide tartrate having a structure as represented by Formula II:

Formula II

2. The tartrate according to claim 1 which is Crystal Form A of the tartrate, characterized in that it has a X-ray powder diffraction pattern with peaks located at positions with 2θ values of about 7.3, 9.6, 11.0, 15.3, 18.1, 18.9, 23.8, 24.5, 26.2, 26.7, and 27.1, a Raman spectrum with peaks located at positions with Raman shift values of about 1613 cm$^{-1}$, 1597 cm$^{-1}$, 1571 cm$^{-1}$, 1543 cm$^{-1}$, 1389 cm$^{-1}$, 827 cm$^{-1}$, and 543 cm$^{-1}$, and a DSC thermogram with a sharp endothermic peak at 238.6° C.

3. The tartrate according to claim 1 which is Crystal Form B of the tartrate, characterized in that it has a X-ray powder diffraction pattern with peaks located at positions with 2θ values of about 8.0, 8.9, 9.5, 10.5, 14.8, 15.3, 16.1, 17.9, 18.9, 24.5, and 26.5, a Raman spectrum with peaks located at positions with Raman shift values of about 1612 cm$^{-1}$, 1596 cm$^{-1}$, 1569 cm$^{-1}$, 1540 cm$^{-1}$, 1519 cm$^{-1}$, 1388 cm$^{-1}$, 1286 cm$^{-1}$, 1259 cm$^{-1}$, 827 cm$^{-1}$, and 543 cm$^{-1}$, and a DSC thermogram with a sharp endothermic peak at 239.9° C.

4. A pharmaceutical formulation comprising 3-(5-fluoro-4-(4-methyl-2-(methylamino) thiazol-5-yl) pyrimidin-2-ylamino)-benzenesulfonamide tartrate and one or more pharmaceutically acceptable excipients.

5. A preparation method of the Crystal Form A of 3-(5-fluoro-4-(4-methyl-2-(methylamino)thiazol-5-yl) pyrimidin-2-ylamino)-benzenesulfonamide tartrate according to claim 2, comprising the following steps:
  (1) adding dimethyl sulfoxide to 3-(5-fluoro-4-(4-methyl-2-(methylamino)thiazol-5-yl)pyrimidin-2-ylamino)-benzenesulfonamide in an amount that is 4 to 8 times that of 3-(5-fluoro-4-(4-methyl-2-(methylamino)thiazol-5-yl)pyrimidin-2-ylamino)-benzenesulfonamide, heating to completely dissolve, and filtering while the liquid is hot;
  (2) adding a certain amount of tartaric acid and water to the first mixture, and reacting to obtain a second mixture; and
  (3) adding a certain amount of a water-miscible solvent to the second mixture, and reacting to obtain 3-(5-fluoro-4-(4-methyl-2-(methylamino)thiazol-5-yl) pyrimidin-2-ylamino)-benzenesulfonamide tartrate, which is the Crystal Form A of the tartrate.

6. The method according to claim 5, wherein the water-miscible solvent in step (3) is an alcohol.

7. The method according to claim 6, wherein the alcohol is ethanol.

8. The method according to claim 5, wherein the second mixture is obtained by mixing tartaric acid and 3-(5-fluoro-4-(4-methyl-2-(methylamino)thiazol-5-yl) pyrimidin-2-ylamino)-benzenesulfonamide at a molar ratio of 1.1 to 1.3:1.

9. A method of treating diseases or conditions caused by proliferative disorders, the method comprising administering to a patient in need thereof the 3-(5-fluoro-4-(4-methyl-2-(methylamino) thiazol-5-yl) pyrimidin-2-ylamino)-benzenesulfonamide tartrate according to claim 1.

10. The method according to claim 9, wherein the diseases or conditions caused by proliferative disorders are cancer.

11. The method according to claim 10, wherein the cancer is leukemia.

12. A use method of treating a disease or condition responsive to the inhibition of a protein kinase, the method comprising administering to a patient in need thereof the 3-(5-fluoro-4-(4-methyl-2-(methylamino) thiazol-5-yl) pyrimidin-2-ylamino)-benzenesulfonamide tartrate according to claim 1.

13. A use method of treating a disease or condition responsive to the inhibition of a protein kinase, the method comprising administering to a patient in need thereof the Crystal Form A of 3-(5-fluoro-4-(4-methyl-2-(methylamino) thiazol-5-yl) pyrimidin-2-ylamino)-benzenesulfonamide tartrate according to claim 2.

14. The method of claim 11, wherein the leukemia is acute myeloid leukemia.

* * * * *